(12) United States Patent
Liu et al.

(10) Patent No.: US 10,188,497 B2
(45) Date of Patent: Jan. 29, 2019

(54) IMPLANT CONVEYING DEVICE AND IMPLANTED MEDICAL INSTRUMENT

(71) Applicant: Lifetech Scientific (Shenzhen) Co., Ltd., Shenzhen (CN)

(72) Inventors: Xiangdong Liu, Shenzhen (CN); Jie Chen, Shenzhen (CN); Zhiwei Zhang, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 146 days.

(21) Appl. No.: 15/108,021

(22) PCT Filed: Nov. 7, 2014

(86) PCT No.: PCT/CN2014/090603
§ 371 (c)(1),
(2) Date: Jun. 24, 2016

(87) PCT Pub. No.: WO2015/101107
PCT Pub. Date: Jul. 9, 2015

(65) Prior Publication Data
US 2016/0317274 A1 Nov. 3, 2016

(30) Foreign Application Priority Data
Dec. 30, 2013 (CN) .......................... 2013 1 0747039

(51) Int. Cl.
*A61F 2/01* (2006.01)
*A61B 17/12* (2006.01)

(52) U.S. Cl.
CPC .......... *A61F 2/01* (2013.01); *A61B 17/12122* (2013.01); *A61B 2017/12054* (2013.01); *A61F 2002/011* (2013.01); *A61F 2220/0075* (2013.01)

(58) Field of Classification Search
CPC ...... A61F 2017/12054; A61F 2002/011; A61F 2220/0075; A61B 2017/00623; A61B 2017/00575
See application file for complete search history.

(56) References Cited

U.S. PATENT DOCUMENTS 5,372,600 A * 12/1994 Beyar ........................ A61F 2/95
606/194
5,456,713 A * 10/1995 Chuter ............... A61B 17/0469
606/194

(Continued)

FOREIGN PATENT DOCUMENTS

CN      1668250 A      9/2005
CN    101933839 A      1/2011

(Continued)

OTHER PUBLICATIONS

Office action in parent priority application 201310747039.5 in China dated Jun. 3, 2015.

(Continued)

*Primary Examiner* — Alexander Orkin
(74) *Attorney, Agent, or Firm* — Raymond Sun (57) ABSTRACT

The present invention relates to an implant conveying device, comprising a pusher (20), a control component (21), a connecting wire (11) and a control wire (4). The pusher (20), of which one end is connected to the control component (21), is provided with a tube cavity (6) and a lock hole (7) communicated with the tube cavity. One end of the control wire (4) is connected to the control component (21), and the other end thereof is driven by the control component to be movably accommodated in the tube cavity (6) of the pusher. One end of the connecting wire (11) is connected to the pusher (20) or to the control component (21), and the other end thereof is used for passing through an implant (1) and then entering the lock hole (7). The control wire (4) is (Continued)

driven by the control component (21) to pass through the connecting wire (11) to connect the implant (1) and the conveying device, or the control wire (4) is driven by the control component (21) to be disengaged from the connecting wire (11) to release the implant (1). By means of the conveying device, locking rings on instruments are removed, so that no redundant metal remains after the implant is implanted into the human body.

17 Claims, 4 Drawing Sheets

(56) References Cited

U.S. PATENT DOCUMENTS

| | | | |
|---|---|---|---|
| 5,554,183 A * | 9/1996 | Nazari | A61F 2/07 623/1.13 |
| 7,550,002 B2 * | 6/2009 | Goto | A61F 2/94 623/1.11 |
| 2002/0165569 A1 * | 11/2002 | Ramzipoor | A61B 17/12022 606/191 |
| 2003/0144673 A1 * | 7/2003 | Onuki | A61B 17/12013 606/139 |
| 2004/0111095 A1 * | 6/2004 | Gordon | A61B 17/3468 606/108 |
| 2006/0036280 A1 * | 2/2006 | French | A61B 17/12022 606/200 |
| 2006/0116714 A1 * | 6/2006 | Sepetka | A61B 17/12022 606/200 |
| 2006/0122647 A1 * | 6/2006 | Callaghan | A61B 17/0057 606/213 |
| 2006/0276826 A1 | 12/2006 | Mitelberg et al. | |
| 2006/0276827 A1 * | 12/2006 | Mitelberg | A61B 17/12022 606/200 |
| 2007/0010850 A1 | 1/2007 | Balgobin | |
| 2007/0112381 A1 | 5/2007 | Figulla | |
| 2007/0135889 A1 * | 6/2007 | Moore | A61F 2/07 623/1.13 |
| 2007/0162048 A1 * | 7/2007 | Quinn | A61B 17/12122 606/113 |
| 2007/0221230 A1 * | 9/2007 | Thompson | A61B 17/12022 128/207.15 |
| 2007/0233223 A1 * | 10/2007 | Styrc | A61F 2/07 623/1.11 |
| 2007/0282373 A1 * | 12/2007 | Ashby | A61B 17/0057 606/213 |
| 2008/0039953 A1 * | 2/2008 | Davis | A61B 17/0057 623/23.76 |
| 2008/0306503 A1 * | 12/2008 | Que | A61B 17/12022 606/191 |
| 2008/0306504 A1 | 12/2008 | Win | |
| 2009/0138023 A1 * | 5/2009 | Johnson | A61B 17/12022 606/108 |
| 2012/0065667 A1 * | 3/2012 | Javois | A61B 17/12122 606/213 |

FOREIGN PATENT DOCUMENTS

| | | |
|---|---|---|
| CN | 103690202 A | 4/2014 |
| CN | 104116574 A | 10/2014 |
| EP | 2 133 043 A1 | 12/2009 |
| WO | WO 2007/070792 A2 | 6/2007 |

OTHER PUBLICATIONS

First office action in corresponding China application No. 201310747039.5.

PCT search report in corresponding PCT application No. PCT/CN2014/090603.

Supplementary European Search report dated Aug. 9, 2017 in corresponding European application No. 14 87 5946.

* cited by examiner

IMPLANT CONVEYING DEVICE AND IMPLANTED MEDICAL INSTRUMENT

TECHNICAL FIELD

The present invention relates to medical instruments, in particular to an implant conveying device and an implanted medical instrument including the conveying device.

BACKGROUND OF THE PRESENT INVENTION

Percutaneous interventional technology is a therapeutic method with an increasingly wider application field. A variety of implants, such as a heart defect occluder, a vascular plug, a vascular filter and the like, may be placed into the heart and the artery and vein vessels of the human body by using catheter interventional therapy.

When these implants are implanted into the heart and the artery and vein vessels of the human body through the catheter interventional method, due to the complex anatomical structures of the heart and the artery and vein vessels of the human body, a catheter, a guide wire and a pusher must be used to ensure that the implant reaches a predetermined position. The catheter first reaches the predetermined position under the guidance of the guide wire. A flexible and fine catheter is required during such an operation, while the catheter and the guide wire are designed to provide good radiopaque characteristics under an X ray, After the catheter reaches the predetermined position, the guide wire is removed, and the implant is then accommodated into the catheter, and guided to the distal end of the catheter by the pusher through a channel established by the catheter. When the implant reaches the distal end of the catheter, the implant is released from the catheter by the pusher, and finally will be disconnected from the pusher, so that the implant is released.

Figure 1:
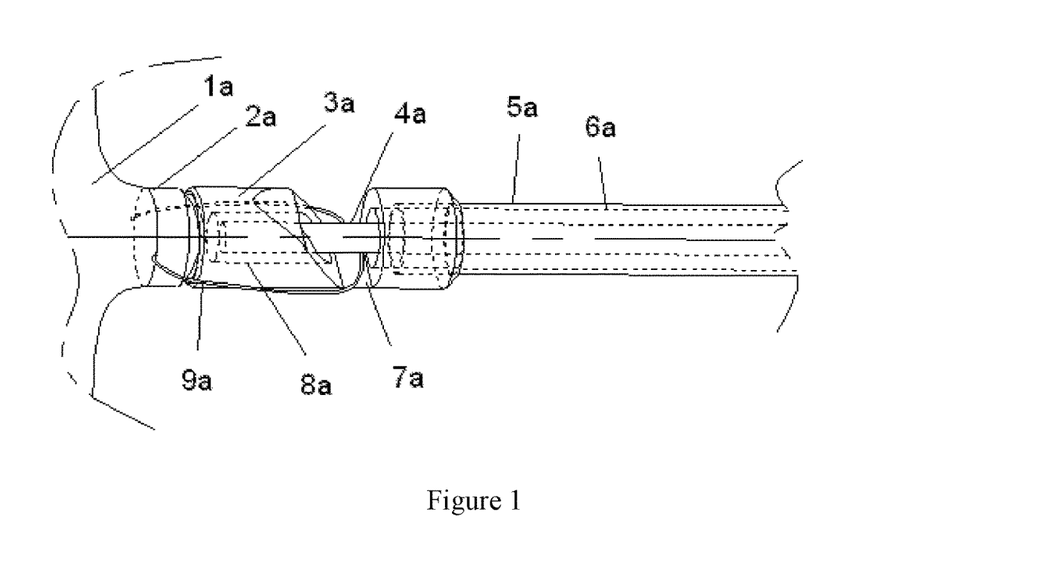
FIG. 1 is a schematic diagram of an implanted medical instrument of the prior art.

In prior implanted medical instruments (hereinafter general terms of implants and pushers), the implants and the pushers are usually in threaded connection or connected by using a connecting wire. For example, a Chinese patent application, of which the application number is 201010265431.2, discloses a device for connecting an implant and a pusher by using a connecting wire. As shown in FIG. 1, the device includes an implant 1a with a closure head 2a, and a pusher 5a; at least one lock ring 9a is arranged on the implant 1a, and a lock 3a having an inner cavity 8a is arranged on the top end of the pusher 5a. The inner cavity 8a of the lock 3a is communicated with a tube cavity 6a of the pusher 5a; the lock 3a is provided with at least one lock hole 7a, and the tube cavity of the pusher 5a is provided with a control wire 4a inside. The control wire 4a, the lock ring 9a and the lock hole 7a are matched with each other to form a plug structure so as to connect the implant with the pusher, and deliver the implant to a predetermined position, wherein the closure head plays the role of fixing the lock ring which plays the role of connecting, and the control wire 4a is withdrawn to achieve release.

The implanted medical instrument mentioned above has the following disadvantages and limitations. 1. The lock ring is formed at the implant; after the implant is implanted into the human body, the lock ring is also implanted into the human body, resulting in the increase in the amount of metal remaining in the human body. This increase of the amount of metal means the increase of the amount of metal elements released in the human body, resulting in unpredictable biological risk, 2. After the implant is implanted into the human body, it is possible that the lock ring and the surface of the implant are not fitted closely; so that the endothelial tissue subsequently may not completely cover the lock ring, thereby resulting in a thrombus source at the implant.

SUMMARY OF THE PRESENT INVENTION

A technical problem to be solved by the present invention is to provide an implanted medical instrument capable of reducing biological risk and avoiding the creation of a thrombus source, and to provide an implant conveying device capable of improving surgical success rate.

A technical solution adopted by the present invention is that an implant conveying device is provided, including a pusher, a control component, a connecting wire and a control wire. The pusher, of which one end is connected to the control component, comprises a tube cavity and a lock hole communicated with the tube cavity; one end of the control wire is connected to the control component, and the other end thereof is capable of being driven by the control component to be movably accommodated in the tube cavity of the pusher. One end of the connecting wire is connected to the pusher or to the control component, and the other end thereof is capable of being used for passing through an implant and then entering the lock hole. The control wire is capable of being driven by the control component to pass through the connecting wire to connect the implant with the conveying device, or the control wire is capable of being driven by the control component to be disengaged from the connecting wire to release the implant.

Preferably, the length of the connecting wire between the implant and the pusher may be adjustable by the control component, when one end of the connecting wire is fixed in the control component.

Preferably, the pusher includes a catheter and a lock, one end of the catheter is connected to the control component; the lock with one end being open includes an inner cavity, the open end is communicated with another end of the catheter; the lock hole is defined in the lock and vertically communicated with the tube cavity.

Preferably, an operating button is arranged on the control component, and one end of the control wire is fixed on the operating button.

Preferably, a restricting mechanism configured to limit the movement of the operating button is arranged on the control component, the restricting mechanism including a security button, a driving member which is in interaction with the security button and provided with a torsion spring, and an elastic stopper which is capable of being driven by the driving member and configured to restrict the movement of the operating button.

Preferably, an unopened end surface of the lock is provided with a groove.

Preferably, a ring is formed on another end of the connecting wire and configured for the control wire to pass therethrough.

Preferably, the lock is provided with an observation hole configured to confirm whether the unopened end of the lock is propped against the control wire.

Preferably, one end of the control wire, which is matched with the connecting wire, is bent into a hook-shaped structure; when connecting the implant conveying device with the implant, the hook-shaped structure hooks the connecting wire in a position where the lock hole is located, and pulls the control wire back to a proximal end; the connection is achieved when the hook-shaped structure leaves the inner cavity of the lock; when the implant is disengaged from the connecting wire, the control wire is pushed until the hook-shaped structure passes through a distal end of the lock hole.

Another technical solution adopted by the present invention is that an implanted medical instrument is provided, including an implant and the implant conveying device mentioned above; the implant has a through hole, another end of the connecting wire passes through the through hole and enters the lock hole, and is sleeved on the control wire; the control wire is capable of being driven by the control component to be disengaged from the connecting wire to release the implant.

Preferably, the implant has a mesh structure and a closure head configured to restrain the mesh structure, the through hole is a gap formed by mutually enclosing the nickel-titanium alloy wires, or a hole formed on the implant. A manufacturing method of the through hole includes a step of: forming a through hole on the implant; or placing a transverse mold bar into a nickel-titanium wire mesh tube during a heat-treatment shaping process; or evenly dividing the nickel-titanium wires to the right and to the left, and binding them into two bundles by using metal wires to form a through hole.

Compared with the prior art, the present invention has the following advantages. 1. The conveying device of the present invention does not need to be additionally provided with a locking ring on the surface of the implant, so that the amount of metal remaining in the human body is reduced after the implant is implanted into the human body, thereby reducing potential biological risk and avoiding a thrombus source for the implant. 2. The length of the connecting wire in the conveying device of the present invention may be freely adjusted during a process of assembling with the lock, so that the difficulty in controlling the length of the locking ring in the production process is reduced, and the production yield in the assembling process is improved.

DETAILED DESCRIPTION OF THE PRESENT INVENTION

In order to make the objectives, the technical solutions and the advantages of the present invention more clear, the present invention will be further described in detail with reference to the accompanying drawings and the embodiments. It should be understood that the specific embodiments described here is merely used for explaining the present invention, but not for limiting the present invention.

Figure 2:
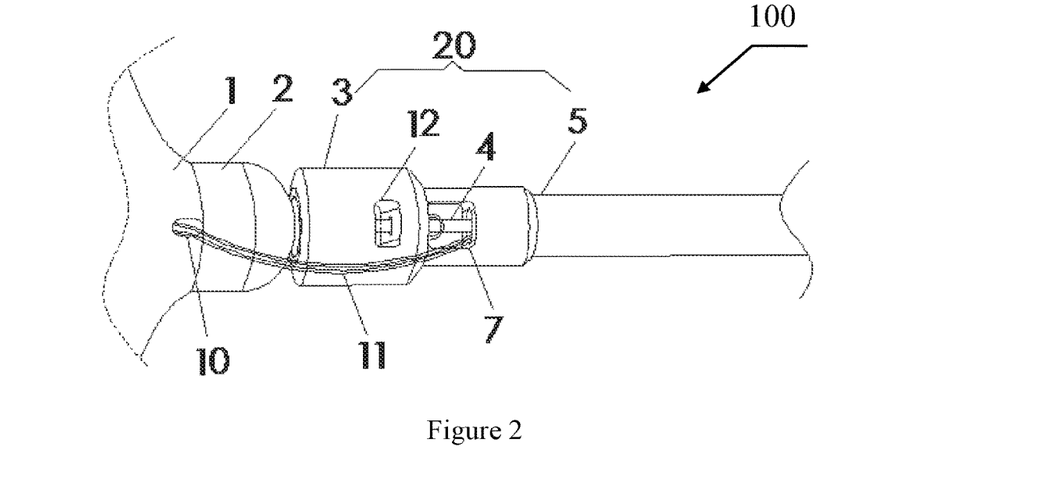
FIG. 2 is a schematic diagram of an implanted medical instrument provided by one embodiment of the present invention.
Figure 3:
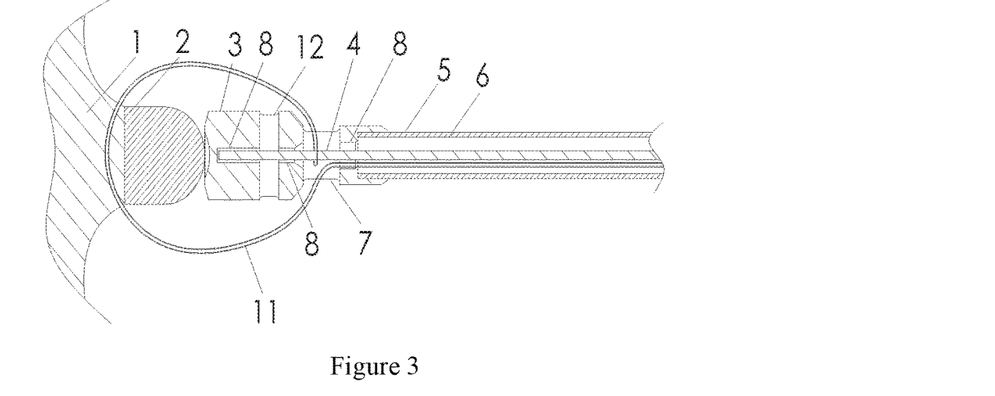
FIG. 3 is a cross-sectional view of FIG. 2.
Figure 10:
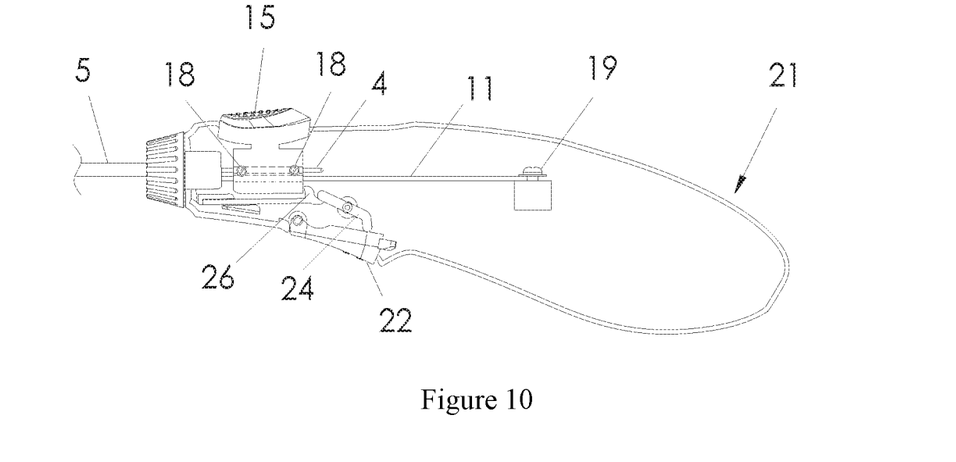
FIG. 10 is a schematic diagram of a control component provided by one embodiment of the present invention.

One embodiment of the present invention provides an implanted medical instrument 100, as shown in FIG. 2, FIG. 3 and FIG. 10, including an implant 1 and a conveying device configured to deliver the implant 1. The conveying device mainly includes a pusher 20 and a control component 21 (as shown in FIG. 10). A through hole is defined at the distal portion of the implant 1. In the embodiment, the implant 1 is a heart occluder. The pusher 20 includes a catheter 5 and a lock 3.

Further as shown in FIG. 4 to FIG. 10, a closure head 2 configured to bring ends of metal wires of the implant 1 together is arranged on an end portion of the implant 1. A through hole 10, through which a connecting wire passes, is defined in a portion of the implant 1, which is near the closure head 2. A lock 3 having an inner cavity 8 is arranged on the top end of the catheter 5. The inner cavity 8 of the lock 3 is communicated with a tube cavity 6 of the catheter 5. At least one lock hole 7 is defined in the lock 3, and a control wire 4 is received in the tube cavity 6 of the catheter 5. The control wire 4, a connecting wire 11 and the lock hole 7 are matched with each other to form a plug structure connection. One end of the connecting wire 11 is fixed on the control component 21, and the connecting wire 11 is wound around a screw 19 (as shown in FIG. 10) and fixed by the screw 19. The length of the connecting wire 11 may be adjusted by rotating the screw 19 so as to adjust a distance between the implant 1 and the lock 3. Another end of the connecting wire 11 extends through the implant 1, meanwhile crosses the closure head 2, and then enters into the lock hole 7, and is finally sleeved on the control wire 4. One end of the control wire 4 is fixed on an operating button 15 on the control component 21, and is fixed by fixing screws 18. The control wire 4 can be actuated by the control component 21 to move in the tube cavity 6 till the other end of the control wire 4 passes through the connecting wire 11 or backtracks to be separated from the connecting wire 11. If there is a need to connect the implant 1 with the catheter 5, one end of the connecting wire 11 passes through the through hole 10 and enters the lock hole 7, and then the operating button 15 is pushed to move towards the direction of the closure head 2 till the control wire 4 passes through the connecting wire 11, As shown in FIG. 10, a restricting mechanism configured to limit the movement of the operating button 15 is arranged on the control component 21, and includes a security button 22, a rotary driving member 24 in contact with the security button 22, and an elastic stopper 26 which is driven by the rotary driving member 24 and configured to restrict the movement of the operating button 15. When the security button 22 is pressed upwards, the rotary driving member 24 is rotated around the center itself, i.e., one end of the rotary driving member 24 in contact with the security button 22 moves upwards, and one end in contact with the elastic stopper 26 moves downwards. Hence, one end of the elastic stopper 26 is oscillated downwards under the pressure of the rotary driving member 24, to release the restriction to the operating button 15.

The restricting mechanism is operated to make the operating button 15 move along the direction away from the catheter 5, thereby ensuring that the control wire 4 is moved along the inner cavity 8 of the lock 3 towards the direction away from the end socket 2 till another end of the control wire 4 is moved into the lock hole 7 and separated from the connecting wire 11. In the absence of any external force, the rotary driving member 24 returns to an initial position under the action of a torsion spring. When the security button 22 is pressed, the security button 22 applies force onto the rotary driving member 24, and the rotary driving member 24 applies force onto the stopper 26, so that the stopper 26 and the operating button 15 are disengaged from each other. When the security button 22 is released, the security button 22 returns to the initial position, and the rotary driving member 24 and the stopper 26 also returns to the initial position.

The control component 21 is operated to press the security button 22 while pushing the operating button 15 along a direction close to the screw 19, thereby ensuring that the control wire 4 is moved along the inner cavity 8 of the lock 3 towards the direction away from the closure head 2 until another end of the control wire 4 is moved into the lock hole 7 and separated from the connecting wire 11; the implant 1 and the catheter 5 are then disengaged.

The implant 1 may also be a vascular plug used for artery and vein blood vessels, and may also be a thrombus filter or other instruments having a tail end. The structures of these instruments are well known by a person of ordinary skill in the art, and are not described in detail here.

A common heart defect occluder or vascular plug is a mesh structure formed by braiding nickel titanium alloy wires, having a closure head 2 on one end. In order to achieve the objective of the embodiment, a through hole 10 may be defined in the nickel-titanium alloy wire (braided wire) close to the closure head 2 by heat-treatment shaping, and there are a variety of methods for shaping the through hole 10; e.g., placing a transverse mold bar into a nickel-titanium wire mesh tube during a heat-treatment shaping step; or evenly dividing the nickel-titanium wires to the right and to the left, and binding them into two bundles by using metal wires to form a through hole. The heat-treatment method is well-known to a person of ordinary skill in the art, and is not described in detail. The through hole 10 may be a gap formed by enclosing nickel-titanium wires mutually, and may also be defined on the implant alone through drilling. Compared with the prior art, since the implant replaces a prior metal lock ring by the through hole, there is no metal brought from the metal lock ring after the implant is implanted into the human body, so that released amount of metal ions is reduced, and the risk that the endothelial tissue may not completely cover the lock ring when the lock ring and the surface of the implant are not fitted closely is also avoided at the same time, thereby reducing thrombus source of the implant.

Figure 4:
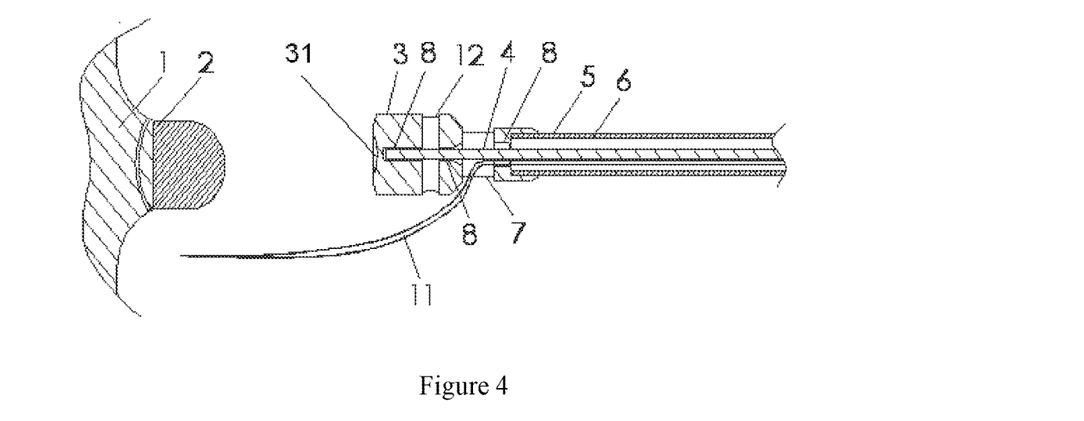
FIG. 4 is a schematic diagram showing the disengagement of a pusher from an implant.

The catheter 5 may be a spring tube formed by densely winding a metal wire, and the lock 3 is welded on the top end of the catheter 5. The lock 3 is provided with the inner cavity 8 and the lock hole 7. The catheter 5 and the lock 3 are coaxial, The inner cavity 8 of the lock 3 is communicated with the tube cavity 6 of the catheter 5. The control wire 4 is received in the tube cavity 6 of the catheter 5. The control wire 4 may move in the tube cavity 6 and the inner cavity 8 along the axial direction, and the top end of the control wire 4 may reach the lock hole 7. A distal diameter of the lock 3 is greater than a difference between an inner diameter of a conveying sheath tube and a diameter of the closure head 2 of the implant 1 to ensure that the implant 1 will not drop out of the lock 3 when it is pushed in the conveying sheath tube, thereby avoiding the difficulty of pushing the implant 1. In this way, the surgical success rate is improved. Of course, in order to ensure proper movement in the sheath, the distal diameter of the lock 3 is also smaller than the inner diameter of the conveying sheath tube at the same time. For example, the diameter of the end socket 2 of the implant 1 is 1.5 mm, the inner diameter of the conveying sheath tube is 3 mm, and the distal diameter of the lock 3 must be greater than 1.5 mm. Meanwhile, for good match between the closure head 2 of the implant 1 and the distal end of the lock 3, a spherical groove 31 may be defined on the distal end of the lock 3 (as shown in FIG. 4), The tube cavity 6 of the catheter 5 is also provided with a connecting wire 11 inside, and the connecting wire 11 may be a polymer wire and may also be multi-strand metal twisted wires, preferably multi-strand nickel-titanium twisted wires in this embodiment. The tail ends of the connecting wire 11 are combined to pass through the inner cavity 6 of the catheter 5 and fixed on the control component 21, so that a ring is formed at the distal end of the connecting wire 11. A distal head of the connecting wire 11 passes through the through hole 10 of the implant 1 and then is passed through by the control wire 4; after passing through the head of the connecting wire 11, the control wire 4 is propped against the bottom of the distal end of the inner cavity 8 of the lock 3, so as to ultimately play a role of connecting the implant 1 with the catheter 5. When the implant 1 and the catheter 5 are connected with each other, the implant 1 under a tensile state should be ensured to directly face the lock 3 of the catheter 5. The distance between the implant 1 and the lock 3 of the catheter 5 may be adjusted and controlled by adjusting the length of the connecting wire 11.

Figure 5:
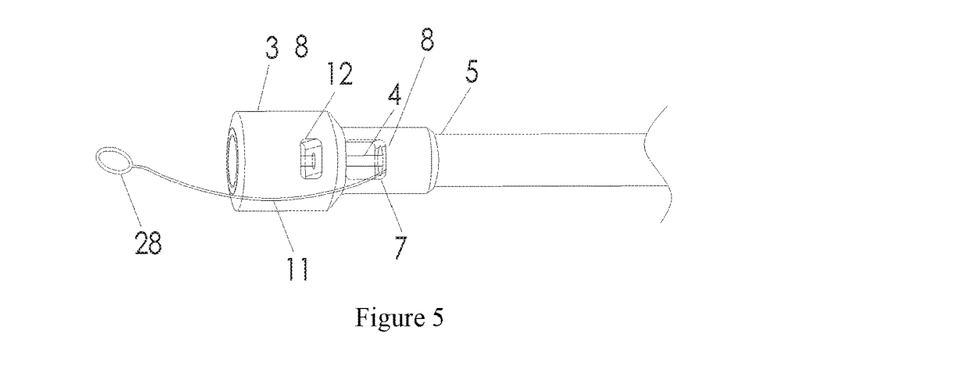
FIG. 5 is a schematic diagram of one end (a free end) of a connecting wire provided by another embodiment of the present invention.

As shown in FIG. 5, in addition to the above structure, the connecting wire 11 may also have other various structures: e.g., a ring structure 28 is additionally arranged on the head of a single connecting wire 11 and may be formed by a variety of ways, such as knotting the head end of the connecting wire 11, or welding a metal ring on the head.

Figure 9:
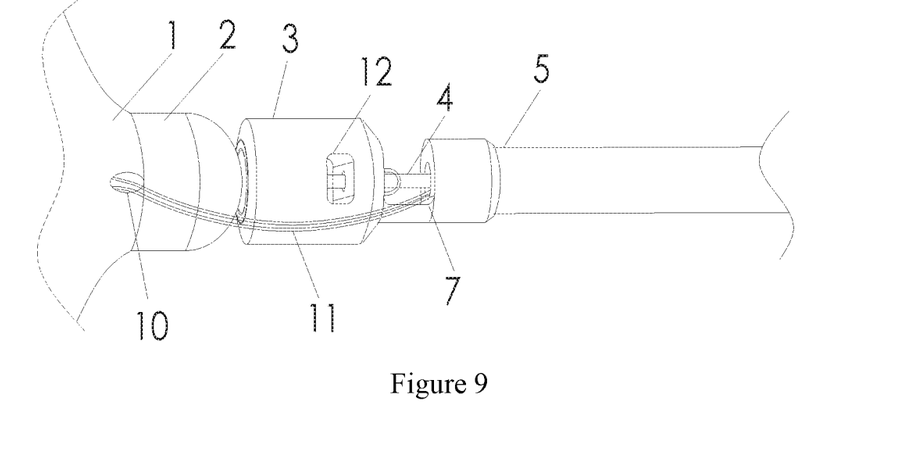
FIG. 9 is a schematic diagram of forming a groove by removing a side wall on one side of a lock hole provided by one embodiment of the present invention.

One end of the lock 3 is connected to the catheter 5. The inner diameter of one end of the lock 3 connected to the catheter 5 is equal to the outer diameter of the catheter 5 to ensure that the catheter 5 may be mounted in the inner cavity of this end of the lock 3, with the connection accomplished preferably by laser welding. Another end of the lock 3 is propped against the closure head 2 of the implant, and the top thereof is closed and also formed with the spherical groove 31 that allows the closure head 2 to rotate by closely fitting to the spherical groove 31. In the present embodiment, the lock hole 7 can be shaped as a through hole, in order to facilitate the assembly, and a side wall on one side of the lock hole 7 may be removed to form a groove, as shown in FIG. 9. The radial size of one end of the lock 3 close to the implant 1 is not less than a difference value between the inner diameter of the conveying sheath applied during surgery and the diameter of the end socket 2, while being less than the inner diameter of the conveying sheath; in this way, when the implant 1 is pushed within the sheath tube, the implant 1 will not drop out of the lock 3, thereby avoiding difficulties in pushing the implant and improving the surgical success rate.

In this embodiment, in order to facilitate welding the lock 3 and the catheter 5, the thickness of an outer wall of a cavity body in one end of the lock 3 connected to the catheter 5 may be adjusted to be a thickness appropriate for intensified welding, and the appropriate thickness is in the range of 0.1 to 0.5 mm.

In order to facilitate assembling the device, the front end of the lock 3 may be additionally provided with an observation hole 12 configured to confirm whether the bottom of the distal end of the inner cavity 8 of the lock 3 is completely propped against the control wire 4.

In order to improve the flexibility of the catheter 5, a certain length of the front end of the catheter 5 may be polished, and the polished length is preferably in a range from 5% to 15% of the total length of the pusher. In order to facilitate manufacturing the catheter 5 by laser welding, while avoiding the situations where the catheter 5 cannot be welded by laser due to the excessive thickness or the catheter being damaged by the laser due to the thickness being too thin, and to ensure the strength of the catheter 5, the preferable thickness range for polishing the catheter 5 should not exceed one half of the wall thickness of the catheter 5. The wall thickness of the catheter 5 is preferably in the range of 0.3 mm to 0.4 mm, and the thickness of the polished segment of the catheter 5 is preferably in the range of 0.2 mm to 0.3 mm.

When there is a need to release the implant 1 during a therapy, the control wire 4 is retracted into the tube cavity 6 of the catheter 5, so that the head of the connecting wire 11 is not restrained by the control wire 4 to be disengaged from the lock hole 7 of the lock 3. At the same time, the catheter 5 is dragged, and the control wire 4 may be withdrawn from the inside of the through hole 10 of the implant 1 so as to completely separate the implant 1 from the catheter 5.

Figure 6:
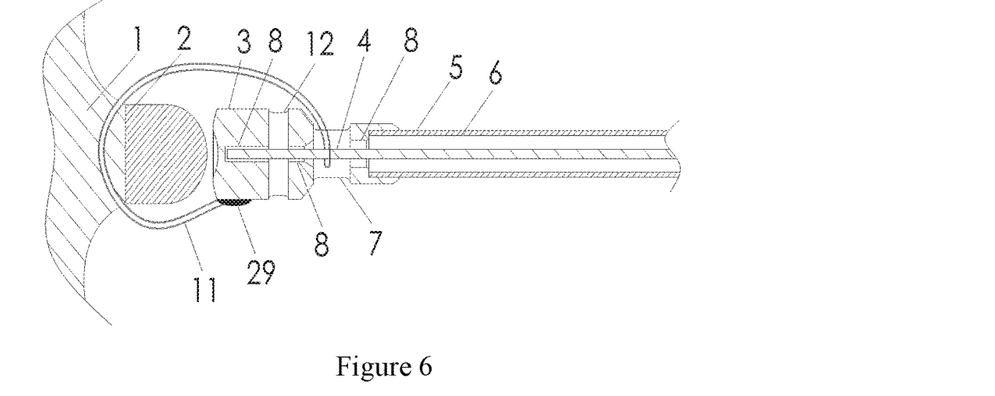
FIG. 6 is a cross-sectional view of a connecting wire welded or fixed to a lock by glue according to still another embodiment of the present invention.
Figure 7:
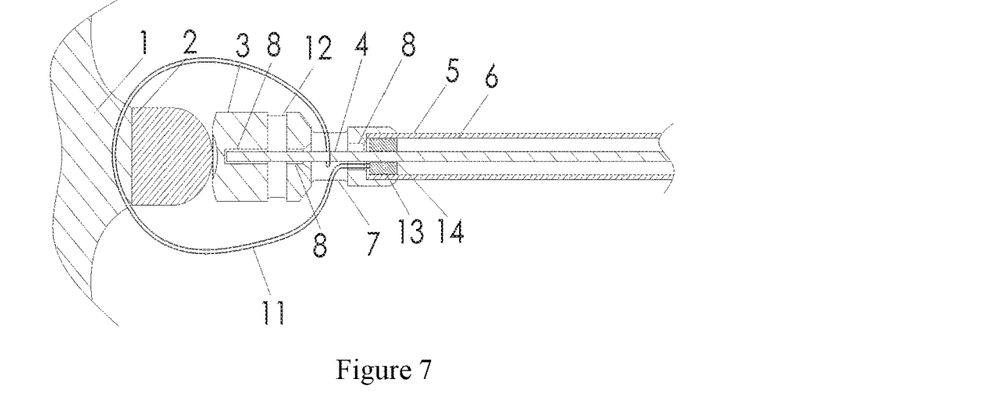
FIG. 7 is a cross-sectional view of a connecting wire fixed on a cylinder according to one embodiment of the present invention.

A second embodiment of the present invention is shown in FIG. 6. The other mechanisms of the second embodiment are the same as those of the first embodiment, except that the fixation manner of the connecting wire is adjusted. As shown in FIG. 6, the fixed end of the connecting wire 11 may be fixed on the side wall of the lock 3 of the catheter 5; when the connecting wire 11 is a metal wire, the connection may be accomplished by laser welding or resistance welding and the like; when the connecting wire 11 is a non-metal wire, the connection may be accomplished by gluing. In FIG. 6, one end of the connecting wire 11 is fixed on a welding spot or a glue dot 29. As shown in FIG. 7, the connecting wire 11 may be fixed on a cylinder 13 by a screw; and the cylinder 13 is placed in the tube cavity 6 of the catheter 5. The cylinder 13, of which the outer diameter is smaller than the diameter of the tube cavity 6 of the catheter 5 and greater than the diameter of the adjacent inner cavity 8 of the lock 3, is a cylindrical member with a central through hole 14, so that the cylinder 13 may be clamped at the distal end of the tube cavity 6 of the catheter 5. Meanwhile, the outer diameter of the central through hole 14 is greater than the diameter of the control wire 4, in order to ensure that the control wire 4 may move inside the through hole 14.

Figure 8:
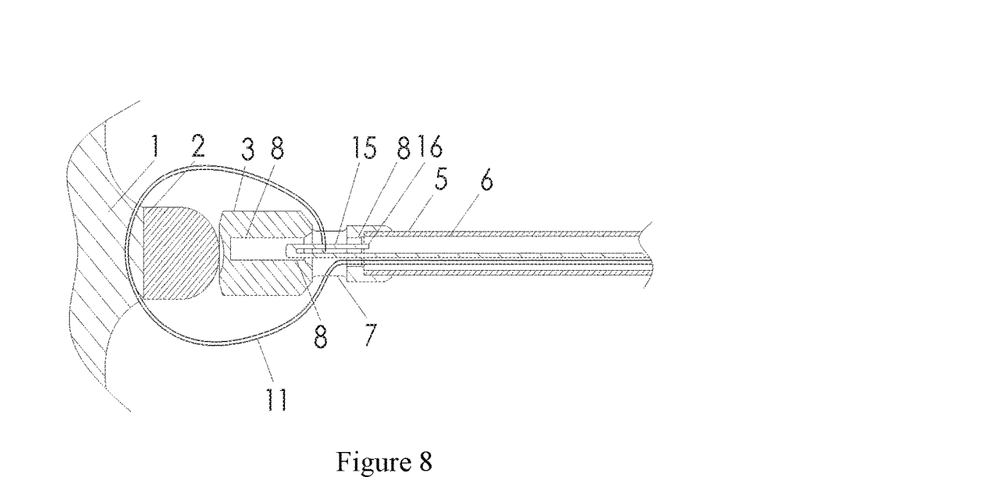
FIG. 8 is a cross-sectional view of a control wire having a hook-shaped structure provided by one embodiment of the present invention.

According to the first embodiment, when the control wire 4 is retracted into the tube cavity 6 of the catheter 5, the connecting wire 11 may be disengaged from the implant 1. In this regard, as a third embodiment of the present invention, as shown in FIG. 8, the control wire 4 in the first embodiment is replaced by a control wire 15 (also referred to as 'hook-shaped control wire') with a hook-shaped structure, and the direction of a hook faces towards the proximal end of the catheter 5. When there is a need to connect the implant 1, the hook-shaped structure 16 of the hook-shaped control wire 15 is first moved to the leftmost end of the inner cavity 8 or moved until the free end of the hook-shaped structure 16 is located on the left side of the tail end of the connecting wire 11, and then is moved to the right (towards the direction of the control component 12), so that the hook-shaped structure 16 of the hook-shaped control wire 15 hooks the ring (or the ring structure) on the front end of the connecting wire 11 and pulls the hook-shaped control wire 15 back to the proximal end (towards the direction of the control component 12). In this way, the hook-shaped control wire 15 and the connecting wire 11 are connected together. If there is a need to disengage the connecting wire 11, the hook-shaped control wire 15 is pushed until the hook-shaped structure 16 moves to pass through the distal end of the lock hole 7, and the hook-shaped structure 16 is disengaged from the ring (or the ring structure) on the front end of the connecting wire 11.

The above descriptions are merely preferred embodiments of the present invention, but not for limiting the present invention. Any modification, equivalent replacement and improvement done within the spirit and principle of the present invention should be regarded as falling into the protection scope of the present invention.

The invention claimed is:

1. An assembly, comprising:
    an implant for occluding a defect, the implant having a meshed body defining a through hole; and
    an implant conveying device for delivering the implant to a treatment location, wherein the conveying device comprises a pusher, a control component, a connecting wire and a control wire;
    the pusher, of which one end is connected to the control component, comprising a tube cavity and a lock hole communicated with the tube cavity;
    one end of the control wire is connected to the control component, and the other end thereof is capable of being driven by the control component to be movably accommodated in the tube cavity of the pusher;
    one end of the connecting wire is connected to the pusher or to the control component, and the other end thereof has a ring that extends through the through hole of the meshed body of the implant and then entering the lock hole; and
    the control wire is capable of being driven by the control component to pass through the ring of the connecting wire to connect the implant with the conveying device, and the control wire is also capable of being driven by the control component to be disengaged from the ring of the connecting wire to release the implant so as to deliver the implant to the treatment location, wherein the conveying device is separated from the implant after the control wire is disengaged from the ring and the connecting wire is removed from the treatment location.

2. The assembly according to claim 1, wherein the length of the connecting wire between the implant and the pusher is adjustable by the control component, when one end of the connecting wire is fixed in the control component.

3. The assembly according to claim 1, wherein the pusher comprises a catheter and a lock, one end of the catheter is connected to the control component, the lock with one end being open comprises an inner cavity, the open end is communicated with another end of the catheter; the lock hole is defined in the lock and vertically communicated with the tube cavity.

4. The assembly according to claim 1, wherein an operating button is arranged on the control component, and one end of the control wire is fixed on the operating button.

5. The assembly according to claim 4, wherein a restricting mechanism configured to restrict the movement of the operating button is arranged on the control component, the restricting mechanism comprises a security button, a driving member which is in interaction with the security button and provided with a torsion spring, and an elastic stopper which is capable of being driven by the driving member and configured to restrict the movement of the operating button.

6. The assembly according to claim 4, wherein an unopened end surface of the lock is provided with a groove.

7. The assembly according to claim 4, wherein the lock is provided with an observation hole configured to confirm whether an unopened end of the lock is completely propped against the control wire.

8. The assembly according to claim 4, wherein one end of the control wire, which is matched with the connecting wire, is bent into a hook-shaped structure; when connecting the implant conveying device with the implant, the hook-shaped structure hooks the connecting wire in a position where the lock hole is located, and pulls the control wire back to a proximal end; wherein the connection is completed when the hook-shaped structure leaves the inner cavity of the lock; when the implant is disengaged from the connecting wire, the control wire is pushed until the hook-shaped structure passes through a distal end of the lock hole.

9. The assembly according to claims 1, wherein a ring is formed on another end of the connecting wire and configured for the control wire passing therethrough.

10. The assembly according to claim 1, wherein the implant has a closure head configured to restrain the meshed body, the through hole is a gap formed by mutually enclosing nickel-titanium alloy wires, or a hole formed on the implant; a manufacturing method of the through hole comprises a step of: forming a through hole on the implant; or placing a transverse mold bar into a nickel-titanium wire mesh tube during a heat-treatment shaping process; or evenly dividing the nickel-titanium wires to the right and to the left, and binding them into two bundles by metal wires to form a through hole.

11. The assembly according to claim 1, wherein the length of the connecting wire between the implant and the pusher is adjustable by the control component, when one end of the connecting wire is fixed in the control component.

12. The assembly according to claim 1, wherein the pusher comprises a catheter and a lock, one end of the catheter is connected to the control component, the lock with one end being open comprises an inner cavity, the open end is communicated with another end of the catheter; the lock hole is defined in the lock and vertically communicated with the tube cavity.

13. The assembly according to claim 1, wherein an operating button is arranged on the control component, and one end of the control wire is fixed on the operating button.

14. The assembly according to claim 13, wherein a restricting mechanism configured to restrict the movement of the operating button is arranged on the control component, the restricting mechanism comprises a security button, a driving member which is in interaction with the security button and provided with a torsion spring, and an elastic stopper which is capable of being driven by the driving member and configured to restrict the movement of the operating button.

15. The assembly according to claim 13, wherein an unopened end surface of the lock is provided with a groove.

16. The assembly according to claim 13, wherein the lock is provided with an observation hole configured to confirm whether an unopened end of the lock is completely propped against the control wire.

17. The assembly according to claim 13, wherein one end of the control wire, which is matched with the connecting wire, is bent into a hook-shaped structure; when connecting the implant conveying device with the implant, the hook-shaped structure hooks the connecting wire in a position where the lock hole is located, and pulls the control wire back to a proximal end; wherein the connection is completed when the hook-shaped structure leaves the inner cavity of the lock; when the implant is disengaged from the connecting wire, the control wire is pushed until the hook-shaped structure passes through a distal end of the lock hole.

* * * * *